United States Patent [19]
Sekine et al.

[11] Patent Number: 6,054,484
[45] Date of Patent: *Apr. 25, 2000

[54] TRANSPARENT AQUEOUS SOLUTION OF DICLOFENAC SODIUM AND MEDICINAL COMPOSITIONS WITH THE USE OF THE SAME

[75] Inventors: Takashi Sekine; Eiji Ogura; Shinichi Ota; Kazuyuki Ishikawa; Takaaki Matsumoto, all of Ami-machi, Japan

[73] Assignees: Tsumura & Co., Tokyo; Oishi Koseido Co., Ltd., Tosu, both of Japan

[ * ] Notice: This patent is subject to a terminal disclaimer.

[21] Appl. No.: 09/125,011

[22] PCT Filed: Feb. 6, 1997

[86] PCT No.: PCT/JP97/00293

§ 371 Date: Aug. 7, 1998

§ 102(e) Date: Aug. 7, 1998

[87] PCT Pub. No.: WO97/28794

PCT Pub. Date: Aug. 14, 1997

[30] Foreign Application Priority Data

Feb. 7, 1996 [JP] Japan .................................. 8-044029
Feb. 7, 1996 [JP] Japan .................................. 8-044030
Feb. 7, 1996 [JP] Japan .................................. 8-044031

[51] Int. Cl.⁷ .................................................. A61K 31/195
[52] U.S. Cl. ............................................................. 514/567
[58] Field of Search ................................................ 514/567

[56] References Cited

U.S. PATENT DOCUMENTS 5,795,916   8/1998   Sekine et al. .

FOREIGN PATENT DOCUMENTS

| 62-153227 | 7/1987 | Japan . |
| 62-228027 | 10/1987 | Japan . |
| 63-8329 | 1/1988 | Japan . |
| WO 96/04902 | 2/1996 | WIPO . |

*Primary Examiner*—William R. A. Jarvis
*Attorney, Agent, or Firm*—Oblon, Spivak, McClelland, Maier & Neustadt, P.C.

[57] ABSTRACT

Disclosed are a clear aqueous solution of diclofenac sodium dissolved in a mixed solvent of a fatty acid dialkylolamide and water; an anti-inflammatory analgesic composition excellent in percutaneous absorption, which comprises the clear aqueous solution and a higher unsaturated aliphatic alcohol contained in the solution; and a self-adhesive cataplasm comprising a cataplasm base and the clear aqueous solution, polybutene and gelatin added in the base. The clear aqueous solution of diclofenac sodium contains, in particular, diclofenac sodium, a fatty acid dialkylolamide and water at a ratio falling within a hexagonal region formed by linking the points A, B, C, D, E and F in the figure.

12 Claims, 1 Drawing Sheet

6,054,484

TRANSPARENT AQUEOUS SOLUTION OF DICLOFENAC SODIUM AND MEDICINAL COMPOSITIONS WITH THE USE OF THE SAME

This application is a 371 of PCT/SP97/00293, filed Feb. 6, 1997.

TECHNICAL FIELD

This invention relates to a clear aqueous solution of diclofenac sodium and a medicinal composition making use of the solution. More specifically, the present invention is concerned with a clear aqueous solution with diclofenac sodium stably dissolved therein, which is useful for the provision of aqueous medicinal preparations and the like; a medicinal composition featuring an increase in percutaneous absorption of the clear aqueous solution without impairment to the solubility of diclofenac sodium; and a self-adhesive cataplasm making use of the aqueous solution and having percutaneous absorption and sufficient adhesiveness.

BACKGROUND ART

Diclofenac sodium is a non-steroidal pharmaceutical having excellent anti-inflammatory analgesic effects and, along with indomethacin having similar drug efficacy, is one of pharmaceuticals which are most widely used. This diclofenac sodium is now furnished or sold on the market only in the unit dosage form of oral preparations and suppositories. When orally administered, non-steroidal anti-inflammatory analgesics such as diclofenac sodium and indomethacin are however known to develop side effects such as gastrointestinal problems depending on the dose. In particular, even if an inflamed part to which administration is intended is a local part such as a joint or a part around the joint, the administration of an oral preparation or a suppository also requires to increase the drug concentrations in parts other than the inflamed part in order to obtain an effective drug concentration in the affected part. This has led to the administration of non-steroidal anti-inflammatory analgesics at excessively high doses, thereby arousing concerns about such side effects as mentioned above.

Research and development work has therefore been conducted on topical dosage forms of non-steroidal anti-inflammatory analgesics. For substances having relatively high lipophilicity such as indomethacin and ketoprofen, topical transdermal preparations such as external liquid preparations, ointments and plasters have already been furnished and are available on the market. Concerning diclofenac sodium, however, it is the current situation that no practically acceptable transdermal preparation is available yet due to difficulty in stably dissolving it in a base.

Described specifically, diclofenac sodium itself has solubility of about 1.5 wt. % (hereinafter referred to simply as "%") in water but, when various base ingredients are added to formulate it into an external medicinal preparation, becomes very prone to crystallization. It is therefore the current situation that no solution of diclofenac sodium is actually available in a form suited for use in the formulation of a medicinal preparation.

As a method for dissolving diclofenac sodium in a solution, there is now known a technique in which diclofenac sodium is dissolved using a lower alcohol such as ethanol or isopropanol and the resulting solution is then formulated into a medicinal preparation. However, a lower alcohol has high volatility and hence involves drawbacks in that it imposes a limitation on the available unit dosage form and tends to cause irritation on skin. Such a lower alcohol is thus not considered to be suitable for the manufacture of medicinal products.

It has therefore been desired to develop a technique that makes it possible to keep diclofenac sodium stably dissolved in water without relying upon such a lower alcohol and even after addition of base ingredient for formulation into a unit dosage form.

DISCLOSURE OF THE INVENTION

Expecting difficulty in keeping diclofenac sodium stably dissolved in water in the presence of base ingredients, the present inventors first attempted to formulate diclofenac sodium into a unit dosage form by dissolving it in oily ingredients. As a matter of fact, indomethacin, ketoprofen and the like are formed into medicinal preparations by dissolving them in an oil ingredient such as mentha oil because they are insoluble in water.

Through the above attempt, however, diclofenac sodium was found to have low solubility in oil ingredients because it is an ionic substance.

In the course of a subsequent screening of solvents for diclofenac sodium, it was luckily found that, as an oil ingredient, coconut fatty acid diethanolamide which does not dissolve diclofenac sodium can dissolve diclofenac sodium at a high concentration and stably when formed into a liquid mixture with water and, moreover, that the resulting aqueous solution of diclofenac sodium is in the form of a colorless, clear, homogeneous, aqueous solution. It was also found that addition of a higher unsaturated aliphatic alcohol to this aqueous solution leads to an improvement in the percutaneous absorption of diclofenac sodium and also allows the resultant mixture to remain in the form of a colorless, clear, homogeneous, gel-like, aqueous solution without precipitation of diclofenac sodium even when sodium polyacrylate and sorbitol, common base ingredients for external preparations, are added to the aqueous solution.

The present invention has been completed based on these findings, and has as a first object thereof the provision of a clear aqueous solution of diclofenac sodium, which comprises diclofenac sodium, a fatty acid dialkylolamide and water.

Another object of the present invention is to provide an anti-inflammatory analgesic composition capable of exhibiting high percutaneous absorption of diclofenac sodium, which comprises the clear aqueous solution and a higher unsaturated aliphatic alcohol contained therein.

A further object of the present invention is to provide a self-adhesive cataplasm obtained by mixing the clear aqueous solution with a cataplasm base and then adding polybutene and gelatin.

BEST MODES FOR CARRYING OUT THE INVENTION

Figure 1:
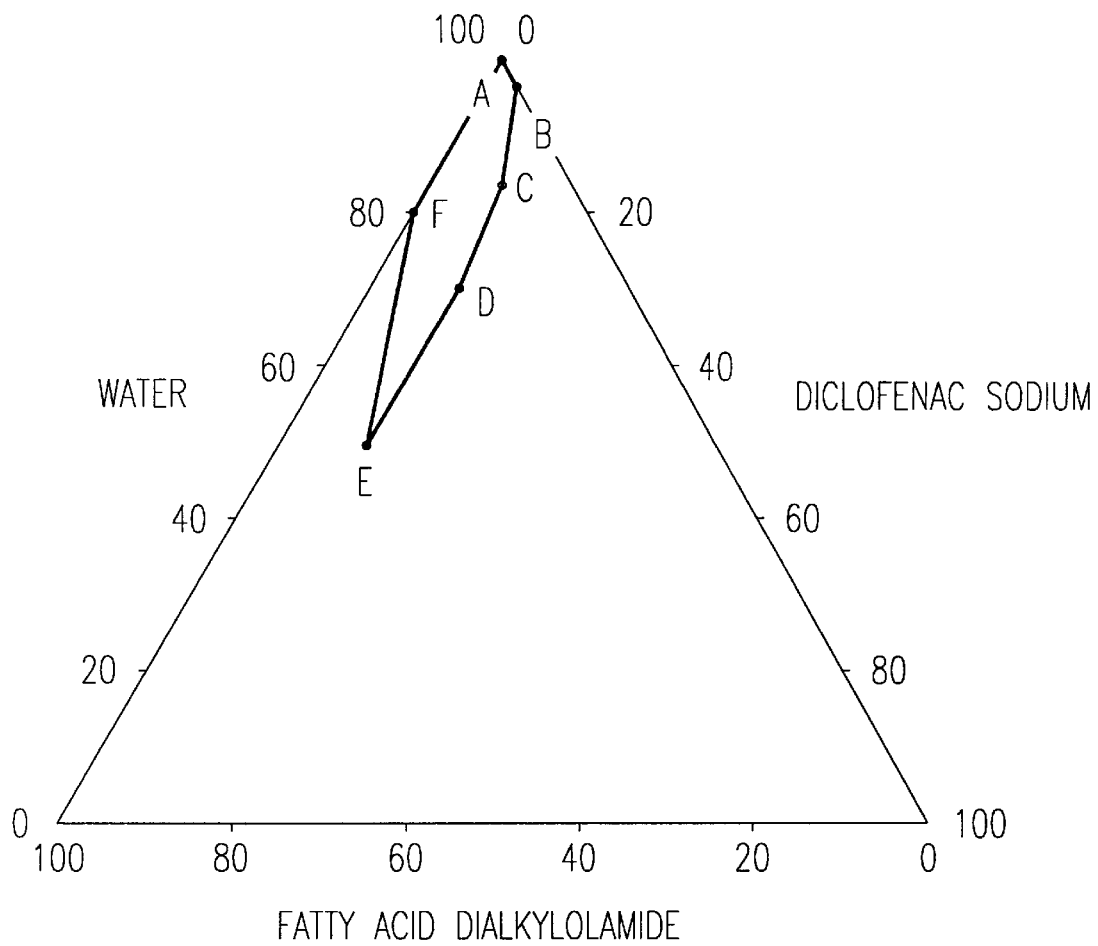
FIG. 1 is a diagram showing a range where clear aqueous solutions are available in a system consisting of diclofenac sodium, a fatty acid dialkylolamide (coconut fatty acid diethanolamide) and water, in which individual points represent point A (0,0,100), point B (1.8,0,98.2), point C (8,8,84), point D (10,20,70), point E (10,40,50) and point F (0,20,80) [the parenthesized values successively indicate the proportions (%) of diclofenac sodium, the fatty acid dialkylolamide (as specified above) and water].

In a first aspect of the present invention (hereinafter called "the first invention"), there is provided a clear aqueous solution of diclofenac sodium, which comprises diclofenac sodium, a fatty acid dialkylolamide and water. To prepare this clear aqueous solution, it is necessary to simply add diclofenac sodium to a liquid mixture of the fatty acid dialkylolamide and water.

A fatty acid dialkylolamide is a compound available by condensation of a fatty acid and a dialkylolamine. Examples of its fatty acid moiety can include coconut oil fatty acid, palm kernel oil fatty acid, palmitic acid, myristic acid, stearic acid, lauric acid, oleic acid, linoleic acid, isostearic acid, capric acid, and caprylic acid. Examples of the dialkylolamine moiety to be condensed can include di(lower alkanol)amines such as diethanolamine and diisopropanolamine. These fatty acid dialkylolamides can be used either singly or in combination.

Illustrative of fatty acid dialkylolamides preferred for use in the clear aqueous solution according in this aspect can be coconut fatty acid diethanolamide, palm kernel fatty acid diethanolamide, stearic acid diethanolamide, lauric acid diethanolamide, oleic acid diethanolamide, linoleic acid diethanolamide and isostearic acid diethanolamide. Of these, particularly preferred is coconut fatty acid diethanolamide.

If a system consists of diclofenac sodium, a fatty acid dialkylolamide and water only in the present invention, provision of a completely clear aqueous solution of diclofenac sodium is feasible when these components fall within particular proportion ranges, respectively.

Described specifically, as will be understood from Examples to be described subsequently herein, such an aqueous solution is available when their proportions fall within a hexagonal area formed by connecting the individual points A (0,0,100), B (1.8,0,98.2), C (8,8,84), D (10,20,70), E (10,40,50) and F (0,20,80) in the ternary phase diagram [the parenthesized values successively indicate the proportions (%) of diclofenac sodium, the fatty acid dialkylolamide and water].

Incidentally, further addition of a solubilizer to a system of diclofenac sodium, a fatty acid dialkylolamide and water makes it possible to expand the area in which clear aqueous solution of diclofenac sodium are available.

Examples of solubilizers usable for the above-mentioned purpose can include lower alcohols such as ethanol and isopropyl alcohol; polyhydric alcohols such as propylene glycol, 1,3-butylene glycol and polyethylene glycol; and nonionic surfactants such as propylene glycol fatty acid esters, glycerin fatty acid esters, sorbitan fatty acid esters, polyoxyethylene sorbitan fatty acid esters, polyethylene glycol fatty acid esters, polyoxyethylene hydrogenated castor oil, polyoxyethylene alkyl ethers, and Pluronic.

These solubilizers can be used in desired proportions to such an extent as not preventing the use of diclofenac sodium as a medicine.

The clear aqueous solution of diclofenac sodium, which can be obtained as described above, is usable for the formulation of various diclofenac-sodium containing medicines, for example, external preparations. This clear aqueous solution of diclofenac sodium features not only its clear external appearance but also its excellent percutaneous absorption of diclofenac sodium through skin probably owing to the dissolution of it.

It is to be noted that even an aqueous solution with diclofenac sodium contained in a form not fully dissolved therein, setting aside the question of external appearance, can still bring about excellent effects from the standpoint of percutaneous absorption because the remaining diclofenac sodium is dissolved in the system of the fatty acid dialkylolamide and water as the percutaneous absorption of diclofenac sodium proceeds.

Illustrative of medicines available from the use of the above-described clear aqueous solution of diclofenac sodium can be external preparations such as lotions, emulsions, suspensions, ointments, gel ointments, gel creams, creams, pastes and cataplasms; oral liquid preparations; and suppositories.

Carriers and additives, which are commonly used in such preparations, can also be used insofar as the advantageous effects of the present invention are not particularly impaired.

Selection of preparation forms such as lotions, gel ointments and gel creams, in particular, out of the above-described preparations is preferred, because such preparations can be imparted with clear appearance and can hence be provided with higher commercial values.

The clear aqueous solution provided in the above-described first invention has no problem in the dissolution of diclofenac sodium. Nonetheless, to use it advantageously as a medicinal composition, it is necessary to formulate it into a composition having still improved percutaneous absorption of diclofenac sodium and excellent utility.

The present inventors therefore proceeded with a search for such a compound that, when added to the clear aqueous solution, can improve the percutaneous absorption of diclofenac sodium without impairing its solubility. As a result, it has been found that higher unsaturated aliphatic alcohols can satisfy these conditions.

A second aspect of the present invention (hereinafter called "the second invention") has been brought to completion through the history as described above. According to the second invention, there is hence provided an anti-inflammatory analgesic composition excellent in percutaneous absorption, which comprises a clear aqueous solution of diclofenac sodium, which comprises diclofenac sodium, water and a fatty acid dialkylolamide, and a higher unsaturated aliphatic alcohol contained therein.

Examples of the higher unsaturated aliphatic alcohol employed in the second invention can include higher unsaturated aliphatic alcohols having 12 to 24 carbon atoms and containing one or more double bonds, such as oleyl alcohol, elaidyl alcohol, linoleyl alcohol and linolenyl alcohol. Their proportions may suitably range from 0.1 to 5% based on the whole base. Addition of the higher unsaturated aliphatic alcohol in an excessively large proportion leads to a reduction in the miscibility with other ingredients, higher tendency of separation and development of skin irritation, whereas its addition in an unduly small proportion cannot bring about sufficient effect for the enhancement of percutaneous absorption.

On the other hand, the clear aqueous solution employed for the formulation of the transdermal composition according to the second invention comprises diclofenac sodium, water and a fatty acid dialkylolamide as described above.

As the fatty acid dialkylol amide out of these ingredients, the above-exemplified fatty acid dialkylol amides are usable. Examples of fatty acid dialkylol amides preferred in this aspect can include coconut fatty acid diethanolamide, palm kernel fatty acid diethanolamide, stearic acid diethanolamide, lauric acid diethanolamide, oleic acid diethanolamide, linoleic acid diethanolamide and isostearic acid diethanolamide. Of these, particularly preferred are coconut fatty acid diethanolamide, lauric acid diethanolamide and stearic acid diethanolamide.

The preferred proportions of the individual ingredients in the composition of transdermal preparation according to the second invention can be from about 0.1 to 5.0% for diclofenac sodium, from about 10 to 96% for water, and from about 0.01 to 10% for the fatty acid dialkylolamide.

The composition of transdermal preparation according to the second invention can be formulated into various forms such as ointments, creams, lotions, emulsions, cataplasms and plasters. Depending on the preparation form, one or more suitable optional ingredients can be added.

Illustrative of optional ingredients which can be added can be alcohols such as ethanol, cetyl alcohol and stearyl alcohol; polyhydric alcohols such as propylene glycol, 1,3-butylene glycol, sorbitol and glycerin; oily ingredients such as palmitic acid, stearic acid, isopropyl myristate, diisopropyl adipate, octyl dodecanol, medium-chain fatty acid triglyceride, diethyl sebacate, olive oil, coconut oil, lanolin, squalane and spermaceti; inorganic fillers such as kaolin, light anhydrous silicic acid, silicon dioxide hydrate, silicic anhydride, magnesium metasilicate aluminate, aluminum hydroxide, aluminum glycinate, talc and titanium oxide; and pH regulators such as tartaric acid, citric acid, malic acid, lactic acid, hydrochloric acid, phosphoric acid, acetic acid, fumaric acid, maleic acid, sodium hydroxide, ammonia, urea, ethylenediamine, diisopropanolamine, diethanolamine, triisopropanolamine and triethanolamine.

To an extent not impairing the solubility and percutaneous absorption, it is also possible to add commonly-employed other ingredients such as high molecular compounds such as gelling agents, tackifier ingredients, antiseptics, antioxidants, perfumes, coloring matters and surfactants.

To use the transdermal composition according to the second invention as a cataplasm plaster, the composition is then coated on a backing such as a film or sheet of a polyolefin, polyester, polyvinylidene chloride, polyurethane, polyvinyl alcohol or polyamide, a non-woven fabric, a cotton fabric or a laminated film or sheet thereof. A sheet of release paper or the like is then applied over a surface of the plaster, whereby a cataplasm is obtained.

In the cataplasm of this invention obtained as described above, diclofenac sodium as the effective ingredient is dissolved in the base and can hence be absorbed well through the skin. By applying the cataplasm to an affected part as needed, anti-inflammatory analgesic effects can be easily obtained.

The cataplasm formulated based on the first invention or the second invention is generally acceptable for its excellent percutaneous absorption and drug efficacy. It is however hardly considered to be satisfactory in the ease of use.

Namely, the clear aqueous solution according to the first invention can prevent crystallization of diclofenac sodium. However, it still cannot be considered to provide a cataplasm which is practically satisfactory in the ease of use, because diclofenac sodium generally reduces the adherability of an adhesive base used in combination and renders insufficient the initial tack and long-lasting adhesiveness of the base of the cataplasm.

A third aspect of the present invention (hereinafter called "the third invention") has been completed to overcome such a problem, and provides a self-adhesive cataplasm comprising a cataplasm base, in which diclofenac sodium, water and a fatty acid dialkylolamide have been added, and polybutene and gelatin.

To practice the third invention, it is indispensable to add both polybutene and gelatin to the base. No sufficient adhesiveness can be obtained if only one of these ingredients is added. Their proportions based on the cataplasm base can be from 0.5 to 5% for polybutene and from 0.5% to 5% for gelatin. Neither polybutene nor gelatin can bring about sufficient adhesiveness when added in a proportion smaller than 0.5%. On the other hand, a proportion greater than 5% leads to an excessively hard plaster as a cataplasm plaster, resulting in difficult spreading work and reduced absorption of diclofenac sodium.

Incidentally, the above-described polybutene is a liquid polymer available by polymerizing isobutylene as a primary component while partially reacting n-butene. One having a molecular weight of from about 400 to 6,000 can be used preferably. Concerning gelatin, on the other hand, one commonly employed in the art can be used. It is possible to use, for example, gelatin having a molecular weight of from about 20,000 to 1,000,000 (on average, 150,000 to 200,000) and jelly strength of from about 80 to 350 bloom.

On the other hand, the base which is used to practice the third invention is one available by adding diclofenac sodium, water and a fatty acid dialkylolamide to a conventional cataplasm base. The preferred proportions of these ingredients in the cataplasm base are from about 0.1 to 5.0% for diclofenac sodium, from about 10 to 70% for water, and from about 0.01 to 10% for the fatty acid dialkylolamide.

As the fatty acid dialkylolamide to be added to the cataplasm base, the above-exemplified fatty acid dialkylolamides can be used. Examples of preferred fatty acid dialkylolamides in this aspect can include coconut fatty acid diethanolamide, palm kernel fatty acid diethanolamide, stearic acid diethanolamide, lauric acid diethanolamide, oleic acid diethanolamide, linoleic acid diethanolamide and isostearic acid diethanolamide. Of these, particularly preferred are coconut fatty acid diethanolamide, lauric acid diethanolamide and stearic acid diethanolamide.

In the above-described cataplasm base, it is possible to include, in addition of the above-described individual ingredients, conventionally-known penetration enhancers, inorganic fillers, pH regulators, polyhydric alcohols, water-soluble high molecular substances, base additives, stabilizers, emulsifiers, antiseptics, solubilizers and the like.

As examples of these additives, the following additives can be mentioned.

Penetration enhancers

Lauryl alcohol, oleyl alcohol, octyl dodecanol, isopropyl myristate, diisopropyl adipate, diethyl sebacate, diisopropyl sebacate, propylene glycol caprate, medium-chain fatty acid triglyceride, squalane, etc.

Inorganic fillers

Kaolin, light anhydrous silicic acid, silicon dioxide hydrate, silicic anhydride, magnesium metasilicate aluminate, aluminum hydroxide, aluminum glycinate, talc, titanium oxide, magnesium hydroxide, synthetic aluminum silicate, bentonite, calcium carbonate, zinc oxide, etc.

pH regulators

Tartaric acid, citric acid, malic acid, lactic acid, hydrochloric acid, phosphoric acid, acetic acid, fumaric acid, maleic acid, sodium hydroxide, ammonia, urea, ethylenediamine, diisopropanolamine, diethanolamine, triisopropanolamine, triethanolamine, etc.

Polyhydric alcohols

Propylene glycol, 1,3-butylene glycol, polyethylene glycol, sorbitol, glycerin, mannitol, etc.

Water-soluble high molecular substances

Carboxymethylcellulose and salts thereof, polyacrylic acid and salts thereof, carboxyvinyl polymers and salts thereof, alginic acid and salts thereof, propylene glycol alginate, chitosan, hydroxypropylcellulose, hydroxypropylmethylcellulose, hydroxyethylcellulose, ethylcellulose, methylcellulose, polyvinyl alcohol, polyvinyl pyrrolidone, N-vinylacetamide polymer, polyvinyl methacrylate, polyethylene glycol, Pluronic, gelatin, methyl vinyl ether-maleic anhydride copolymer, soluble starch, pullulan, a copolymer of methyl acrylate and 2-ethylhexyl acrylate, etc.

Stabilizers

Sodium edetate, citric acid, sodium citrate, oxybenzone, ascorbic acid, tocopherol, dibutylhydroxy-toluene, butylhydroxyanisole, propyl gallate, sodium hydrogensulfite, etc.

Surfactants

Lecithin, lecithin derivatives, propylene glycol fatty acid esters, glycerin fatty acid esters, sorbitan fatty acid esters, polyoxyethylene sorbitan fatty acid esters, polyethylene glycol fatty acid esters, polyoxyethylene hydrogenated caster oil, polyoxyethylene alkyl ethers, Pluronic, etc.

Antiseptics

Parabens such as methylparaben, ethylparaben and propylparaben; benzyl alcohol; benzalconium chloride; benzethonium chloride; chlorobutanol; etc.

Solubilizers

Lower alcohols such as ethanol and isopropyl alcohol.

The self-adhesive cataplasm according to the present invention can be obtained by adding polybutene and gelatin to the above-described cataplasm base, thoroughly mixing the resultant paste, spreading the paste on a backing, and then applying a sheet of release paper or the like over a surface of the plaster.

No particular limitation is imposed on the backing of the cataplasm. Illustrative can be films or sheets of polyolefin, polyester, polyvinylidene chloride, polyurethane, polyvinyl alcohol, polyamide or the like, non-woven fabrics, cotton fabrics, and laminated films or sheets thereof.

In the self-adhesive cataplasm available from the practice of the third invention, diclofenac sodium as the effective ingredient is dissolved in the plaster and can be absorbed well through the skin. It is only necessary to simply apply the self-adhesive cataplasm to an affected part.

EXAMPLES

The present invention will next be described in detail by the following Examples and Preparation Examples. It is however to be borne in mind that the present invention is by no means limited by or to them.

Example I-1

Solubility Test (1)

Compositions were formulated with the proportions of diclofenac sodium, a fatty acid alkylolamide (coconut fatty acid diethanolamide) and water varied as shown below in Table 1. Subsequent to storage at 25° C. for 24 hours, the states of the solutions were visually investigated. The results are shown in Table 1 and FIG. 1.

TABLE 1

| Comp'n No. | Diclofenac sodium | Fatty acid alkylolamide | Water | Dissolved state* |
|---|---|---|---|---|
| 1 | 1.5 | 1.0 | 98.5 | A |
| 2 | 1.5 | 2.0 | 97.5 | A |
| 3 | 1.5 | 4.0 | 94.5 | A |
| 4 | 2.0 | 1.0 | 97.0 | A |
| 5 | 3.0 | 2.0 | 95.0 | A |
| 6 | 3.0 | 10.0 | 87.0 | A |
| 7 | 5.0 | 1.0 | 94.0 | B |
| 8 | 5.0 | 2.0 | 93.0 | B |
| 9 | 5.0 | 4.0 | 91.0 | B |
| 10 | 5.0 | 5.0 | 90.0 | A |
| 11 | 5.0 | 10.0 | 85.0 | A |
| 12 | 5.0 | 20.0 | 75.0 | A |
| 13 | 5.0 | 30.0 | 65.0 | C |
| 14 | 10.0 | 10.0 | 80.0 | C |
| 15 | 10.0 | 20.0 | 70.0 | A |
| 16 | 10.0 | 40.0 | 50.0 | A |
| 17 | 10.0 | 50.0 | 40.0 | C |
| 18 | 20.0 | 10.0 | 70.0 | C |
| 19 | 20.0 | 30.0 | 50.0 | C |
| 20 | 20.0 | 50.0 | 30.0 | C |
| 21 | 30.0 | 10.0 | 60.0 | C |
| 22 | 30.0 | 50.0 | 20.0 | C |

*Each dissolved state was ranked in accordance with the following standard:
A: Completely dissolved.
B: Dissolved when formulated, but after left over, crystals precipitated to some extent.
C: Not fully dissolved.

Example I-2

Solubility Test (2)

Invention compositions and comparative compositions, which are shown below in Table 2 and Table 3, respectively, were formulated. Subsequent to storage at 25° C. for 24 hours, the states of the solutions were visually investigated. The results are shown in Table 4.

TABLE 2

| Ingredient | Invention composition | | | | | | | Control composition |
|---|---|---|---|---|---|---|---|---|
| | 1 | 2 | 3 | 4 | 5 | 6 | 7 | |
| Diclofenac sodium | 5 | 5 | 5 | 5 | 5 | 5 | 5 | 5 |
| Coconut fatty acid diethanolamide | 2 | 2 | 2 | 2 | 2 | 2 | 2 | 2 |
| Purified water | 88 | 88 | 88 | 88 | 88 | 88 | 88 | 93 |
| Polyethylene glycol | 5 | — | — | — | — | — | — | — |
| 1,3-Butylene glycol | — | 5 | — | — | — | — | — | — |
| Ethanol | — | — | 5 | — | — | — | — | — |
| Isopropanol | — | — | — | 5 | — | — | — | — |
| POE hydrogenated castor oil[1] | — | — | — | — | 5 | — | — | — |
| POE layryl ether[2] | — | — | — | — | — | 5 | — | — |
| Pluronic F68[3] | — | — | — | — | — | — | 5 | — |

(Note)
Values indicate proportions (%).
[1]"HCO-60" (product of Nikko Chemicals Co., Ltd.)
[2]"BL-9EX" (product of Nikko Chemicals Co., Ltd.)
[3]Product of Asahi Denka Kogyo K.K.

TABLE 3

|  | Comparative composition | | | | | | |
|---|---|---|---|---|---|---|---|
| Ingredient | 1 | 2 | 3 | 4 | 5 | 6 | 7 |
| Diclofenac sodium | 5 | 5 | 5 | 5 | 5 | 5 | 5 |
| Coconut fatty acid diethanolamide | — | — | — | — | — | — | — |
| Purified water | 90 | 90 | 90 | 90 | 90 | 90 | 90 |
| Polyethylene glycol | 5 | — | — | — | — | — | — |
| 1,3-Butylene glycol | — | 5 | — | — | — | — | — |
| Ethanol | — | — | 5 | — | — | — | — |
| Isopropanol | — | — | — | 5 | — | — | — |
| POE hydrogenated castor oil[1)] | — | — | — | — | 5 | — | — |
| POE layryl ether[2)] | — | — | — | — | — | 5 | — |
| Pluronic F68[3)] | — | — | — | — | — | — | 5 |

(Note)
Values indicate proportions (%).
[1), 2), 3)]Same as in Table 2

TABLE 4

(Results)

| Composition | Dissolved state* | Composition | Dissolved state* |
|---|---|---|---|
| Invention Composition 1 | A | Comparative Composition 1 | C |
| Invention Composition 2 | A | Comparative Composition 2 | C |
| Invention Composition 3 | A | Comparative Composition 3 | C |
| Invention Composition 4 | A | Comparative Composition 4 | C |
| Invention Composition 5 | A | Comparative Composition 5 | C |
| Invention Composition 6 | A | Comparative Composition 6 | C |
| Invention Composition 7 | A | Comparative Composition 7 | C |
| Control Composition | B | | |

*Each dissolved state was ranked as in Table 1 under Example I-1.

Example I-3

Lotion

A water-based clear lotion was obtained in accordance with the following formula and procedures.

(Formula)

|  | Proportion (%) |
|---|---|
| Diclofenac sodium | 2 |
| Coconut fatty acid diethanolamide | 2 |
| Purified water | 73 |
| Oleyl alcohol | 1 |
| D-sorbitol | 20 |
| Hydroxypropylcellulose | 2 |

(Procedures)

The diclofenac sodium and coconut fatty acid diethanolamide were added to the purified water and the resultant mixture was stirred, whereby a clear aqueous solution with the diclofenac sodium dissolved therein was obtained. The oleyl alcohol, D-sorbitol and hydroxypropylcellulose were added to and dissolved in the clear aqueous solution. The resultant water-based lotion was clear.

Example I-4

Gel Preparation

A clear gel preparation was obtained in accordance with the following formula and procedures.

(Formula)

|  | Proportion (%) |
|---|---|
| Diclofenac sodium | 2 |
| Coconut fatty acid diethanolamide | 2 |
| Purified water | 60 |
| Oleyl alcohol | 1 |
| D-sorbitol | 20 |
| Sodium polyacrylate | 5 |
| Propylene glycol | 10 |

(Procedures)

The diclofenac sodium and coconut fatty acid diethanolamide were added to the purified water and the resultant mixture was stirred, whereby a clear aqueous solution with the diclofenac sodium dissolved therein was obtained. The oleyl alcohol and D-sorbitol were added to and dissolved in the clear aqueous solution. A solution of the sodium polyacrylate uniformly suspended in the propylene glycol was added further. The thus-obtained mixture was stirred, whereby a gel preparation was obtained. The gel preparation was clear because the diclofenac sodium was in a dissolved state.

Example I-5

Cataplasm

A cataplasm was formulated in accordance with the following formula and procedures.

(Formula)

|  |  | Proportion (%) |
|---|---|---|
| A | Diclofenac sodium | 2.0 |
|  | Coconut fatty acid diethanolamide | 2.0 |
|  | Purified water | 33.65 |
| B | Gelatin | 3.0 |
|  | Purified water | 12.0 |

-continued

|   | | Proportion (%) |
|---|---|---|
| C | D-sorbitol | 30.0 |
|   | Light anhydrous silicic acid | 2.0 |
| D | Oleyl alcohol | 1.0 |
|   | Propylene glycol | 7.0 |
|   | Sodium polyacrylate | 5.0 |
|   | Sodium carboxymethylcellulose | 1.0 |
|   | Polybutene | 1.0 |
|   | Tartaric acid | 0.15 |
|   | Aluminum hydroxide | 0.2 |

(Procedures)

The ingredients A were mixed, whereby a clear aqueous solution of the diclofenac sodium was obtained. The ingredients B were next heated in a separate container so that a gelatin solution was obtained. The ingredients A, B and C were combined, to which a liquid mixture of the ingredients D was added under stirring to obtain a homogeneous gel. This gel was spread on a non-woven fabric, whereby a cataplasm was obtained.

Example II-1

Skin Penetration Test (1)

Test compositions (ointments) of the formulations shown below in Table 5 were formulated.

After each Wistar male rat (7 weeks old) was shaved at his abdominal part, a piece of skin as large as 2.7 cm in diameter was excised. The thus-excised skin was mounted on a Frantz cell, and 2 g of one of the above preparations were placed on a donor side. A receiver side was filled with a phosphate buffer (pH 7.2). Solutions of the pharmaceutical were sampled at predetermined time intervals from the receiver side, and the amounts of penetrated diclofenac sodium were determined by high-performance liquid chromatography. From the data so obtained, a cumulative penetrated amount ($\mu$g/cm$^2$) and a flux ($\mu$g/cm$^2$/hr) were calculated.

The results are shown below in Table 6.
(Test compositions)

TABLE 5

| Ingredient | Invention Product 8 | Invention Product 9 | Comprative Product 8 |
|---|---|---|---|
| Diclofenac sodium | 2 | 2 | 2 |
| Coconut fatty acid diethanolamide | 2 | 2 | 2 |
| Purified water | 70 | 60 | 71 |
| D-sorbitol | 20 | 20 | 20 |
| Sodium polyacrylate | 5 | 5 | 5 |
| Oleyl alcohol | 1 | 1 | — |
| propylene glycol | — | 10 | — |

(unit: wt. %)

(Results)

TABLE 6

|   | Test composition | | |
|---|---|---|---|
|   | Invention Product 8 | Invention Product 9 | Comprative Product 8 |
| Cumulative penetrated amount ($\mu$g/cm$^2$) | | | |
| At the start | 0 | 0 | 0 |
| 2 hours later | 4.32 | 1.33 | 1.22 |
| 4 hours later | 35.64 | 27.07 | 15.17 |
| 6 hours later | 102.3 | 76.61 | 38.31 |
| 8 hours later | 175.7 | 154.7 | 74.16 |
| 10 hours later | 253.4 | 254.1 | 119.1 |
| Flux ($\mu$g/cm$^2$/hr) | 36.4 | 38.0 | 17.4 |

Example II-2

Skin Penetration Test (2)

Compositions (ointments) of the formulations shown below in Table 7 were formulated. In a similar manner as in Example II-1, the skin penetration of diclofenac sodium was investigated. The results are shown in Table 8.

TABLE 7

|   | Invention Product | Invention composition | | | | | | |
|---|---|---|---|---|---|---|---|---|
| Ingredient | 10 | 9 | 10 | 11 | 12 | 13 | 14 | 15 |
| Diclofenac sodium | 2.0 | 2.0 | 2.0 | 2.0 | 2.0 | 2.0 | 2.0 | 2.0 |
| Coconut fatty acid diethanolamide | 2.0 | 2.0 | 2.0 | 2.0 | 2.0 | 2.0 | 2.0 | 2.0 |
| Purified water | 59.9 | 60.9 | 59.9 | 59.9 | 59.9 | 59.9 | 59.9 | 59.9 |
| D-sorbitol | 20.0 | 20.0 | 20.0 | 20.0 | 20.0 | 20.0 | 20.0 | 20.0 |
| Sodium polyacrylate | 5.0 | 5.0 | 5.0 | 5.0 | 5.0 | 5.0 | 5.0 | 5.0 |
| Tartaric acid | 0.1 | 0.1 | 0.1 | 0.1 | 0.1 | 0.1 | 0.1 | 0.1 |
| 1,3-Butylene glycol | 10.0 | 10.0 | 10.0 | 10.0 | 10.0 | 10.0 | 10.0 | 10.0 |
| Oleyl alcohol | 1.0 | — | — | — | — | — | — | — |
| Isopropyl myristate | — | — | 1.0 | — | — | — | — | — |
| Isopropyl adipate | — | — | — | 1.0 | — | — | — | — |
| Squalane | — | — | — | — | 1.0 | — | — | — |
| Octyl dodecanol | — | — | — | — | — | 1.0 | — | — |
| Medium-chain fatty acid triglyceride | — | — | — | — | — | — | 1.0 | — |
| Diethyl sebacate | — | — | — | — | — | — | — | 1.0 |

TABLE 8

(Results)

| Test composition | Elapsed time (hr) | | | | | |
|---|---|---|---|---|---|---|
| | 0 | 2 | 4 | 5.5 | 7 | 8.5 | 10 |
| Invention Product 10 | 0 | 4.8 | 25.8 | 52.8 | 92.0 | 155.9 | 222.0 |
| Comparative Product 9 | 0 | 0 | 0 | 2.0 | 5.3 | 12.6 | 17.3 |
| Comparative Product 10 | 0 | 0 | 6.8 | 14.0 | 25.2 | 50.5 | 78.5 |
| Comparative Product 11 | 0 | 0 | 5.7 | 12.5 | 20.4 | 28.9 | 43.6 |
| Comparative Product 12 | 0 | 0 | 4.3 | 9.6 | 14.7 | 21.5 | 35.8 |
| Comparative Product 13 | 0 | 0 | 5.7 | 11.3 | 20.5 | 33.8 | 54.6 |
| Comparative Product 14 | 0 | 0 | 2.3 | 6.0 | 11.3 | 20.1 | 28.9 |
| Comparative Product 15 | 0 | 0 | 4.3 | 11.0 | 17.1 | 29.0 | 41.9 |

[Values in the table indicate cumulative penetrated amounts ($\mu g/cm^2$).]

Example II-3

Ointment

In accordance with the following formula, a diclofenac-sodium-containing ointment was formulated by procedures known per se in the art.

Formula

| (Ingredient) | Proportion (%) |
|---|---|
| Diclofenac sodium | 5 |
| Lauric acid diethanolamide | 4 |
| Purified water | 61.84 |
| Oleyl alcohol | 1 |
| "Polysorbate 60" | 3 |
| Cetanol | 4 |
| Stearyl alcohol | 5 |
| Medium-chain fatty acid triglyceride | 6 |
| D-sorbitol | 10 |
| Butylhydroxyanisole | 0.01 |
| Methylparaben | 0.1 |
| Propylparaben | 0.05 |

Example II-4

Lotion

In accordance with the following formula, a diclofenac-sodium-containing lotion was formulated by procedures known per se in the art.

Formula

| (Ingredient) | Proportion (%) |
|---|---|
| Diclofenac sodium | 5 |
| Coconut fatty acid diethanolamide | 10 |
| Purified water | 80 |
| Oleyl alcohol | 5 |

Example II-5

Lotion

In accordance with the following formula, a diclofenac-sodium-containing lotion was formulated by procedures known per se in the art.

Formula

| (Ingredient) | Proportion (%) |
|---|---|
| Diclofenac sodium | 7 |
| Lauric acid diethanolamide | 5 |
| Coconut fatty acid diethanolamide | 5 |
| Purified water | 75.8 |
| Oleyl alcohol | 3 |
| Hydroxypropylcellulose | 0.5 |
| "Pluronic F68" | 1 |
| Propylene glycol | 2 |
| Oxybenzone | 0.5 |
| Methylparaben | 0.15 |
| Propylparaben | 0.05 |

Example II-6

Lotion

In accordance with the following formula, a diclofenac-sodium-containing lotion was formulated by procedures known per se in the art.

Formula

| (Ingredient) | Proportion (%) |
|---|---|
| Diclofenac sodium | 0.5 |
| Coconut fatty acid diethanolamide | 2 |
| Purified water | 95.3 |
| Oleyl alcohol | 1 |
| Polyvinyl alcohol | 0.5 |
| "Polysorbate 60" | 0.5 |
| Methylparaben | 0.15 |
| Propylparaben | 0.05 |

Example II-7

Ointment

In accordance with the following formula, a diclofenac-sodium-containing ointment was formulated by procedures known per se in the art.

Formula

| (Ingredient) | Proportion (%) |
|---|---|
| Diclofenac sodium | 3 |
| Lauric acid diethanolamide | 4 |
| Purified water | 52.3 |
| Oleyl alcohol | 1 |
| Glycerin | 5 |
| Isopropyl alcohol | 30 |
| Hydroxyethylcellulose | 2 |
| Methylcellulose | 2 |
| Oxybenzone | 0.5 |
| Methylparaben | 0.15 |
| Propylparaben | 0.05 |

Example II-8

Cataplasm

In accordance with the following formula, a diclofenac-sodium-containing cataplasm was formulated by procedures known per se in the art.

Formula

| (Ingredient) | Proportion (%) |
| --- | --- |
| Diclofenac sodium | 2 |
| Coconut fatty acid diethanolamide | 2 |
| Purified water | 46.35 |
| Oleyl alcohol | 1 |
| 1,3-Butylene glycol | 10 |
| D-sorbitol solution (70%) | 30 |
| Sodium polyacrylate | 4 |
| Sodium carboxymethylcellulose | 1 |
| Polybutene | 1 |
| Light anhydrous silicic acid | 2 |
| Tartaric acid | 0.15 |
| Aluminum glycinate | 0.5 |

Example II-9

Cataplasm

In accordance with the following formula, a diclofenac-sodium-containing cataplasm was formulated by procedures known per se in the art.

Formula

| (Ingredient) | Proportion (%) |
| --- | --- |
| Diclofenac sodium | 1 |
| Lauric acid diethanolamide | 4 |
| Purified water | 54.75 |
| Oleyl alcohol | 1 |
| Propylene glycol | 7 |
| 1,3-Butylene glycol | 3 |
| D-sorbitol | 20 |
| Sodium polyacrylate | 5 |
| Hydroxypropylmethylcellulose | 1 |
| Gelatin | 1 |
| Light anhydrous silicic acid | 2 |
| Tartaric acid | 0.15 |
| Aluminum hydroxide | 0.1 |

Example III-1

Manufacture of Cataplasm

In accordance with formulas indicated below, cataplasms were manufactured as invention products and comparative products, respectively. Concerning the formulas, Table 9 shows the invention products while Table 10 presents the comparative products.

(Invention Product 11)

In a beaker, diclofenac sodium, coconut fatty acid diethanolamide and purified water were placed in amounts corresponding to their proportions shown in Table 9. They were stirred, whereby a solution with the diclofenac sodium dissolved therein was obtained (Solution A).

In another beaker, gelatin in an amount corresponding to its proportion in Table 9 was dissolved in warm water or hot water, so that a solution with the gelatin dissolved therein was obtained (Solution B).

In a further beaker, sodium polyacrylate, sodium carboxymethylcellulose, tartaric acid, aluminum hydroxide gel, polybutene and oleyl alcohol were dispersed in amounts corresponding to their proportions in Table 9, whereby a liquid mixture was obtained (Solution C).

Solution A, Solution B, a D-sorbitol solution and light anhydrous silicic acid were mixed under stirring with a spatula. Solution C was then gradually added, whereby 1 kg of a homogeneous cataplasm base was obtained.

The thus-obtained cataplasm base was spread on a non-woven fabric and then covered with a plastic film, whereby a cataplasm was obtained.

(Invention Product 12)

A cataplasm was manufactured by similar procedures as in the manufacture of Invention Product 11 except that lauric acid diethanolamide was used in place of coconut fatty acid diethanolamide.

(Invention Products 13–15)

Cataplasms were manufactured by similar procedures as in the manufacture of Invention Product 11 except that the proportion of sodium polyacrylate was reduced to 3.0% and polyvinyl alcohol, hydroxypropylmethylcellulose or N-vinylacetamide polymer was used in a proportion of 1.0%.

(Comparative Product 16)

A cataplasm was manufactured by similar procedures as in the manufacture of Invention Product 11 except that polybutene was not used and the proportion of purified water was adjusted accordingly.

(Comparative Product 17)

A cataplasm was manufactured by similar procedures as in the manufacture of Invention Product 11 except that gelatin was not used and the proportion of purified water was adjusted accordingly.

(Comparative Products 18–26)

Cataplasms were manufactured by similar procedures as in the manufacture of Invention Product 11 except that high molecular substances commonly known as adhesive bases (in Table 10, from "Nikazol TS-620" to sodium caseinate) were used in place of gelatin and polybutene.

TABLE 9

| | Invention Product | | | | |
| --- | --- | --- | --- | --- | --- |
| Ingredient | 11 | 12 | 13 | 14 | 15 |
| Diclofenac sodium | 1.5 | 1.5 | 1.5 | 1.5 | 1.5 |
| Coconut fatty acid diethanolamide | 2.0 | — | 2.0 | 2.0 | 2.0 |
| Lauric acid diethanolamide | — | 2.0 | — | — | — |
| Propylene glycol | 10.0 | 10.0 | 10.0 | 10.0 | 10.0 |
| Oleyl alcohol | 1.0 | 1.0 | 1.0 | 1.0 | 1.0 |
| D-sorbitol (70%) | 40.0 | 40.0 | 40.0 | 40.0 | 40.0 |
| Sodium polyacrylate | 3.0 | 3.0 | 3.0 | 3.0 | 3.0 |
| Sodium carboxymethylcellulose | 1.0 | 1.0 | 1.0 | 1.0 | 1.0 |
| Polyvinyl alcohol | — | — | 1.0 | — | — |
| Sodium hydroxypropylmethylcellulose | — | — | — | 1.0 | — |

TABLE 9-continued

| | Invention Product | | | | |
|---|---|---|---|---|---|
| Ingredient | 11 | 12 | 13 | 14 | 15 |
| N-vinylacetamide polymer | — | — | — | — | 1.0 |
| Light anhydrous silicic acid | 2.0 | 2.0 | 2.0 | 2.0 | 2.0 |
| Tartaric acid | 0.15 | 0.15 | 0.15 | 0.15 | 0.15 |
| Aluminum hydroxide gel | 0.20 | 0.20 | 0.20 | 0.20 | 0.20 |
| Polybutene | 1.0 | 1.0 | 1.0 | 1.0 | 1.0 |
| Gelatin | 3.0 | 3.0 | 3.0 | 3.0 | 3.0 |
| Purified water | Balance | Balance | Balance | Balance | Balance |

TABLE 10

| | COMPARATIVE PRODUCT | | | | | | | | | | |
|---|---|---|---|---|---|---|---|---|---|---|---|
| Ingredient | 16 | 17 | 18 | 19 | 20 | 21 | 22 | 23 | 24 | 25 | 26 |
| Diclofenac sodium | 1.5 | 1.5 | 1.5 | 1.5 | 1.5 | 1.5 | 1.5 | 1.5 | 1.5 | 1.5 | 1.5 |
| Coconut fatty acid diethanolamide | 2.0 | 2.0 | 2.0 | 2.0 | 2.0 | 2.0 | 2.0 | 2.0 | 2.0 | 2.0 | 2.0 |
| Propylene glycol | 10.0 | 10.0 | 10.0 | 10.0 | 10.0 | 10.0 | 10.0 | 10.0 | 10.0 | 10.0 | 10.0 |
| Oleyl alcohol | 1.0 | 1.0 | 1.0 | 1.0 | 1.0 | 1.0 | 1.0 | 1.0 | 1.0 | 1.0 | 1.0 |
| D-sorbitol (70%) | 40.0 | 40.0 | 40.0 | 40.0 | 40.0 | 40.0 | 40.0 | 40.0 | 40.0 | 40.0 | 40.0 |
| Sodium polyacrylate | 4.0 | 4.0 | 4.0 | 4.0 | 4.0 | 4.0 | 4.0 | 4.0 | 4.0 | 4.0 | 4.0 |
| Sodium carboxymethylcellulose | 1.0 | 1.0 | 1.0 | 1.0 | 1.0 | 1.0 | 1.0 | 1.0 | 1.0 | 1.0 | 1.0 |
| Light anhydrous silicic acid | 2.0 | 2.0 | 2.0 | 2.0 | 2.0 | 2.0 | 2.0 | 2.0 | 2.0 | 2.0 | 2.0 |
| Tartaric acid | 0.15 | 0.15 | 0.15 | 0.15 | 0.15 | 0.15 | 0.15 | 0.15 | 0.15 | 0.15 | 0.15 |
| Aluminum hydroxide gel | 0.20 | 0.20 | 0.20 | 0.20 | 0.20 | 0.20 | 0.20 | 0.20 | 0.20 | 0.20 | 0.20 |
| Polybutene | — | 1.0 | — | — | — | — | 1.0 | 1.0 | 1.0 | 1.0 | 1.0 |
| Gelatin | 3.0 | — | — | — | — | — | — | — | — | — | — |
| "Nikazol TS-620"* | — | — | — | 1.0 | — | — | — | — | — | — | — |
| Hydroxypropylmethylcellulose | — | — | — | — | 1.0 | — | — | — | — | — | — |
| Sodium alginate | — | — | — | — | — | 1.0 | — | — | — | — | — |
| Starch acrylate | — | — | — | — | — | — | 1.0 | — | — | — | — |
| "Primal N-580 NF"** | — | — | — | — | — | — | — | 3.0 | — | — | — |
| Carboxylvinyl polymer | — | — | — | — | — | — | — | — | 0.1 | — | — |
| N-vinylacetamide polymer | — | — | — | — | — | — | — | — | — | 3.0 | — |
| Sodium caseinate | — | — | — | — | — | — | — | — | — | — | 3.0 |
| Purified water | Balance | Balance | Balance | Balance | Balance | Balance | Balance | Balance | Balance | Balance | Balance |

*Emulsion of a copolymerized resin of methyl acrylate and 2-ethylhexyl acrylate
**Copolymer of methyl acrylate and n-butyl acrylate

| [Rank] | [Description] |
|---|---|
| A | Remained firmly adherent to the finger. |
| B | Felt sticky although a little weak. |
| C | Separated easily. |

(2) Ranking of long-lasting adhesiveness

Each cataplasm as large as 10×14 cm was applied to a knee of a human subject so that longer sides of the cataplasm extend in the same direction as the leg. The cataplasm was ranked "A" when remained adherent for 8 hours or longer, or ranked "B" when separated before that time.

Example III-2

Adhesiveness Test of Cataplasms

With respect to the cataplasms obtained as Invention Products 11–15 and Comparative Products 16–26 in Example III-1, their adhesiveness was ranked by investigating their initial tack and long-lasting adhesiveness. Concerning the initial tack, adherability and feeling upon application were both investigated. The results are shown in Table 11.

(1) Ranking of initial tack

Adhesion test

Each cataplasm as large as 10×14 cm was applied to an arm, and the arm was then twisted to make the cataplasm face downward. The cataplasm was ranked "B" when fell down, or was ranked "A" when remained adherent.

Organoleptic test

A finger was pressed downwardly against the plaster of each cataplasm and was then lifted. Stickiness felt at that time was ranked in accordance with the following standard.

TABLE 11

| | (Results) | | |
|---|---|---|---|
| Cataplasm | Arm-adhesion initial tack test | Organoleptic initial tack test | 8-Hour adhesion test |
| Invention Product 11 | A | A | A |
| Invention Product 12 | A | A | A |
| Invention Product 13 | A | A | A |
| Invention Product 14 | A | A | A |
| Invention Product 15 | A | A | A |
| Comparative Product 16 | A | B | A |
| Comparative Product 17 | A | A | B |
| Comparative Product 18 | B | C | B |
| Comparative Product 19 | B | C | B |
| Comparative Product 20 | B | C | B |
| Comparative Product 21 | B | C | B |
| Comparative Product 22 | A | A | B |
| Comparative Product 23 | A | A | B |
| Comparative Product 24 | A | A | B |
| Comparative Product 25 | A | A | B |
| Comparative Product 26 | A | A | B |

Example III-3

Drug Efficacy Test of Cataplasms

Using a paw edema model induced by carrageenin on rats, a diclofenac sodium cataplasm according to the present invention (Invention Product 11) and a commercial indomethacin preparation ("Catolep", trade name; product of Sumitomo Pharmaceuticals Company Limited) were compared with each other in anti-inflammatory effects. An application area of each preparation was set as wide as 3×3.9 cm, and anti-inflammatory effects were indicated in terms of swelling inhibition rate (%) upon elapsed time of 3 hours after the administration of carrageenin. As a control, a swelling inhibition rate (%) achieved without application of any cataplasm was used. The results are shown below in Table 12.

TABLE 12

| Invention Product 11 | Comparative Product ("Catlep") | Control |
|---|---|---|
| 39.9 | 17.3 | 1.3 |

As is apparent from the above results, the self-adhesive cataplasm according to the present invention had excellent anti-inflammatory effects compared with the indomethacin preparation already available on the market (comparative product).

Example III-4

Cataplasms having the formulas in Table 13, in which the proportions of polybutene and gelatin were varied, were manufactured. The thus-obtained cataplasms all had excellent self-adhesiveness and percutaneous absorption.

TABLE 13

| | Invention Product | | | | | |
|---|---|---|---|---|---|---|
| Ingredient | 16 | 17 | 18 | 19 | 20 | 21 |
| Diclofenac sodium | 1.5 | 1.5 | 1.5 | 1.5 | 1.5 | 1.5 |
| Coconut fatty acid diethanolamide | 2.0 | 2.0 | 2.0 | 2.0 | 2.0 | 2.0 |
| Propylene glycol | 10.0 | 10.0 | 10.0 | 10.0 | 10.0 | 10.0 |
| Oleyl alcohol | 1.0 | 1.0 | 1.0 | 1.0 | 1.0 | 1.0 |
| D-sorbitol (70%) | 40.0 | 40.0 | 40.0 | 40.0 | 40.0 | 40.0 |
| Sodium polyacrylate | 4.0 | 4.0 | 4.0 | 4.0 | 4.0 | 4.0 |
| Sodium carboxymethylcellulose | 1.0 | 1.0 | 1.0 | 1.0 | 1.0 | 1.0 |
| Light anhydrous silicic acid | 2.0 | 2.0 | 2.0 | 2.0 | 2.0 | 2.0 |
| Tartaric acid | 0.15 | 0.15 | 0.15 | 0.15 | 0.15 | 0.15 |
| Aluminum hydroxide gel | 0.20 | 0.20 | 0.20 | 0.20 | 0.20 | 0.20 |
| Polybutene | 0.5 | 2.0 | 5.0 | 1.0 | 1.0 | 1.0 |
| Gelatin | 3.0 | 3.0 | 3.0 | 0.5 | 2.0 | 5.0 |
| Purified water | Balance | Balance | Balance | Balance | Balance | Balance |

Example III-5

Cataplasms in Table 14 were obtained, in which the penetration enhancer had been changed from oleyl alcohol to other compounds, respectively. The thus-obtained cataplasms all had excellent self-adhesiveness and percutaneous absorption.

TABLE 14

| | Invention Product | | | |
|---|---|---|---|---|
| Ingredient | 22 | 23 | 24 | 25 |
| Diclofenac sodium | 1.5 | 1.5 | 1.5 | 1.5 |
| Coconut fatty acid diethanolamide | 2.0 | 2.0 | 2.0 | 2.0 |
| Propylene glycol | 10.0 | 10.0 | 10.0 | 10.0 |
| Diisopropyl adipate | 1.0 | — | — | — |
| Isopropyl myristate | — | 1.0 | — | — |
| Diethyl sebacate | — | — | 1.0 | — |
| Octyl dodecanol | — | — | — | 1.0 |
| D-sorbitol (70%) | 40.0 | 40.0 | 40.0 | 40.0 |
| Sodium polyacrylate | 4.0 | 4.0 | 4.0 | 4.0 |
| Sodium carboxymethylcellulose | 1.0 | 1.0 | 1.0 | 1.0 |
| Light anhydrous silicic acid | 2.0 | 2.0 | 2.0 | 2.0 |
| Tartaric acid | 0.15 | 0.15 | 0.15 | 0.15 |
| Aluminum hydroxide gel | 0.20 | 0.20 | 0.20 | 0.20 |
| Polybutene | 1.0 | 1.0 | 1.0 | 1.0 |
| Gelatin | 3.0 | 3.0 | 3.0 | 3.0 |
| Purified water | Balance | Balance | Balance | Balance |

Example III-6

Cataplasm

A cataplasm was formulated in accordance with the following formula and procedures.

(Formula)

| | | Proportion (%) |
|---|---|---|
| A | Diclofenac sodium | 2.0 |
| | Coconut fatty acid diethanolamide | 2.0 |
| | Purified water | 33.65 |
| B | Gelatin | 3.0 |
| | Purified water | 12.0 |
| C | D-sorbitol | 30.0 |
| | Light anhydrous silicic acid | 2.0 |

-continued

|   | | Proportion (%) |
|---|---|---|
| D | Oleyl alcohol | 1.0 |
|   | Propylene glycol | 7.0 |
|   | Sodium polyacrylate | 5.0 |
|   | Sodium carboxymethylcellulose | 1.0 |
|   | Polybutene | 1.0 |
|   | Tartaric acid | 0.15 |
|   | Aluminum hydroxide | 0.2 |

(Procedures)

The ingredients A were mixed, whereby a clear aqueous solution of the diclofenac sodium was obtained. The ingredients B were next heated in a separate container so that a gelatin solution was obtained. The ingredients A, B and C were combined, to which a liquid mixture of the ingredients D was added under stirring to obtain a homogeneous gel. This gel was spread on a non-woven fabric, whereby a cataplasm was obtained.

Example III-7

Cataplasm

A cataplasm was formulated in accordance with the following formula and procedures.

(Formula)

|   | | Proportion (%) |
|---|---|---|
| A | Diclofenac sodium | 1.5 |
|   | Coconut fatty acid diethanolamide | 1.5 |
|   | Purified water | 34.65 |
| B | Gelatin | 3.0 |
|   | Purified water | 12.0 |
| C | D-sorbitol | 30.0 |
|   | Light anhydrous silicic acid | 2.0 |
| D | Oleyl alcohol | 1.0 |
|   | 1,3-Butylene glycol | 7.0 |
|   | Sodium polyacrylate | 5.0 |
|   | Sodium carboxymethylcellulose | 1.0 |
|   | Polybutene | 1.0 |
|   | Tartaric acid | 0.15 |
|   | Aluminum hydroxide | 0.2 |

(Procedures)

The ingredients A were mixed, whereby a clear aqueous solution of the diclofenac sodium was obtained. The ingredients B were next heated in a separate container so that a gelatin solution was obtained. The ingredients A, B and C were combined, to which a liquid mixture of the ingredients D was added under stirring to obtain a homogeneous gel. This gel was spread on a non-woven fabric, whereby a cataplasm was obtained.

Example III-8

Cataplasm

A cataplasm was formulated in accordance with the following formula and procedures.

(Formula)

|   | | Proportion (%) |
|---|---|---|
| A | Diclofenac sodium | 1.0 |
|   | Coconut fatty acid diethanolamide | 1.5 |
|   | Purified water | 32.15 |
| B | Gelatin | 3.0 |
|   | Purified water | 12.0 |
| C | D-sorbitol | 30.0 |
|   | Light anhydrous silicic acid | 2.0 |
| D | Oleyl alcohol | 1.0 |
|   | 1,3-Butylene glycol | 10.0 |
|   | Sodium polyacrylate | 5.0 |
|   | Sodium carboxymethylcellulose | 1.0 |
|   | Polybutene | 1.0 |
|   | Tartaric acid | 0.15 |
|   | Aluminum hydroxide | 0.2 |

(Procedures)

The ingredients A were mixed, whereby a clear aqueous solution of the diclofenac sodium was obtained. The ingredients B were next heated in a separate container so that a gelatin solution was obtained. The ingredients A, B and C were combined, to which a liquid mixture of the ingredients D was added under stirring to obtain a homogeneous gel. This gel was spread on a non-woven fabric, whereby a cataplasm was obtained.

INDUSTRIAL APPLICABILITY

The clear aqueous solution of diclofenac sodium according to the first invention of the present application features not only stable dissolution of diclofenac sodium but also its percutaneous absorption improved over the same compound in an undissolved form.

Accordingly, the clear aqueous solution according to the present invention can be used by itself as liquid preparations for external application and oral administration and, moreover, can also be combined with other known pharmaceutical carriers into various medicinal preparations.

Formulation into lotions, gel ointments, gel creams and the like by making use of its clear external appearance can provide clear preparations containing diclofenac sodium, which have heretofore been unavailable. It is therefore possible to bring about improvements not only in pharmacological effects but also in commercial value.

Further, the transdermal composition according to the second invention of the present application contains diclofenac sodium in a dissolved form and also permits its improved percutaneous absorption. The transdermal composition can be advantageously used as diclofenac sodium preparations of the topical dosage form, for example, in various unit dose forms such as ointments, creams, lotions, emulsions, cataplasm plasters and plasters.

In addition, the self-adhesive cataplasm according to the third invention of the present application permits good absorption of diclofenac sodium, and has adhesiveness of such extent as not separating from the skin even when no other securement means is used. The self-adhesive cataplasm can therefore be used extremely advantageously as a transdermal preparation of diclofenac sodium.

What is claimed is:

1. A clear aqueous solution of diclofenac sodium, comprising diclofenac sodium, a fatty acid dialkylolamide and water.

2. A clear aqueous solution of diclofenac sodium, comprising diclofenac sodium, a fatty acid dialkylolamide and water in proportions which all with a hexagonal area formed by connecting point A, point B, point C, point D, point E and point F in FIG. 1.

3. A clear aqueous solution of diclofenac sodium, comprising a liquid composition, which comprises diclofenac sodium, a fatty acid dialkylolamide and water, and a solubilizer added therein.

4. The clear aqueous solution according to claim 3, wherein said solubilizer is a lower alcohol, polyhydric alcohol or nonionic surfactant.

5. The clear aqueous solution according to claim 1, wherein said fatty acid dialkylolamide is coconut fatty acid diethanolamide.

6. An external dermal preparation comprising a clear aqueous solution of diclofenac sodium as defined in claim 1.

7. The external dermal preparation according to claim 6, which is a lotion, emulsion, suspension, ointment, gel ointment, cream, paste or cataplasm.

8. A method for dissolving diclofenac sodium, comprising combining diclofenac sodium, a fatty acid dialkylolamide and water in proportions which fall within a hexagonal area formed by connecting point A, point B, point C, point D, point E, and point F in FIG. 1.

9. An anti-inflammatory analgesic composition excellent in percutaneous absorption, comprising a liquid composition, which comprises diclofenac sodium, water and a fatty acid dialkylolamide, and a higher unsaturated aliphatic alcohol contained therein.

10. The anti-inflammatory analgesic composition according to claim 9, wherein said higher unsaturated aliphatic alcohol is oleyl alcohol.

11. The anti-inflammatory analgesic composition according to claim 9, which is selected from the group consisting of ointments, creams, lotions, emulsions, cataplasms and plasters.

12. A self-adhesive cataplasm comprising a cataplasm, which is composed of a cataplasm base and diclofenac sodium, water and a fatty acid dialkylolamide added in said base, and polybutene and gelatin.

* * * * *